US006048305A

United States Patent [19]

Bauman et al.

[11] Patent Number: 6,048,305

[45] Date of Patent: Apr. 11, 2000

[54] APPARATUS AND METHOD FOR AN OPEN EAR AUDITORY PATHWAY STIMULATOR TO MANAGE TINNITUS AND HYPERACUSIS

[75] Inventors: Natan Bauman, New Haven, Conn.; Roger P. Juneau, Destrehan, La.

[73] Assignee: Natan Bauman, New Haven, Conn.

[21] Appl. No.: 09/131,035

[22] Filed: Aug. 7, 1998

Related U.S. Application Data

[60] Provisional application No. 60/054,942, Aug. 7, 1997.

[51] Int. Cl.$^{7}$ .......... A61B 5/00

[52] U.S. Cl. .......... 600/25; 600/27; 600/28

[58] Field of Search .......... 600/25; 128/746; 381/60, 68.4

[56] References Cited

U.S. PATENT DOCUMENTS

| | | | |
|---|---|---|---|
| 3,764,748 | 10/1973 | Branch et al. . | |
| 4,222,393 | 9/1980 | Hocks et al. . | |
| 4,226,248 | 10/1980 | Manoli . | |
| 4,680,798 | 7/1987 | Neumann | 381/68.4 |
| 4,735,968 | 4/1988 | Guth . | |
| 4,759,070 | 7/1988 | Voroba et al. | 381/60 |
| 4,870,688 | 9/1989 | Voroba et al. | 381/60 |
| 4,954,486 | 9/1990 | Guth . | |
| 4,956,391 | 9/1990 | Sapse . | |
| 4,984,579 | 1/1991 | Burgert et al. . | |
| 5,024,612 | 6/1991 | van den Honert et al. . | |
| 5,064,858 | 11/1991 | Sapse . | |
| 5,167,236 | 12/1992 | Junker | 128/746 |
| 5,279,292 | 1/1994 | Baumann et al. . | |
| 5,325,872 | 7/1994 | Westermann . | |
| 5,403,262 | 4/1995 | Gooch . | |
| 5,563,140 | 10/1996 | Ehrenberger et al. . | |
| 5,589,183 | 12/1996 | Jannetta . | |
| 5,628,330 | 5/1997 | Upham . | |

*Primary Examiner*—Max Hindenburg
*Assistant Examiner*—Brian Szmal
*Attorney, Agent, or Firm*—Bachman & LaPointe, P.C.

[57] ABSTRACT

An open-in-the-ear auditory pathway stimulator device includes a noise generator in the device for generating noise and controls in the device for adjusting the volume of the noise. The device is preferably open ear. The device is preferably programmable. The device can also include a hearing aid for amplifying ambient sounds.

14 Claims, 12 Drawing Sheets

APPARATUS AND METHOD FOR AN OPEN EAR AUDITORY PATHWAY STIMULATOR TO MANAGE TINNITUS AND HYPERACUSIS

CROSS-REFERENCE TO RELATED APPLICATIONS

Priority of U.S. Provisional Patent Application Serial No. 60/054,942, filed Aug. 7, 1997, and incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to an Auditory Pathway Stimulator for management through central habituation of patients suffering from Tinnitus or Hyperacusis, or both. More particularly, the present invention relates to a system and method for reducing the debilitating effects of tinnitus by means of an all-in-the-canal, open-ear, noise stimulus of the auditory pathway.

2. General Background of the Invention

Tinnitus is a wide spread auditory symptom affecting approximately 17% of the general population growing to 33% in the elderly. This percentage translates to about 44 million people in the United States. Most who experience tinnitus manage well, in that it is not disruptive in daily life. However, approximately 25% of people experiencing tinnitus are encumbered to the extent that they actively seek help. The above statistics correspond to approximately 10 million sufferers in the United States and 2 million of these sufferers are debilitated by tinnitus to the point of total disruption of the quality of life (Jastreboff P. J., Gray W. C., and Gold S. L.: "Neurophysiological Approach to Tinnitus Patients", *The American Journal of Otology,* 17:236–340 ©1996). In fact, some extreme cases have led to suicide. At present, there is no cure for tinnitus. Most sufferers are told by medical and audiological professionals they should "learn to live with it."

Over 300 research projects funded by public and private agencies have been conducted to address tinnitus and its harmful effects during the last two decades. A cure is still unforeseen in the near future. This invention is an important step to a systematic solution with long-term significant results.

The concept of tinnitus is difficult to convey since it is a "Phantom Auditory Perception" representing lack of certain neuro activity in the auditory system rather than an increased activity. It is also a symptom associated with many auditory and non auditory pathologies.

Unmanageable tinnitus is due to a conditioned reflex between the central auditory pathways and the limbic system. In short, when the auditory brainstem detects a new sound such as tinnitus it automatically assigns high priority to the new auditory signal. This detection in turn provokes a negative emotional association in the limbic system producing a very strong conditioned reflex perceived as a thread which activates the body's fight-or-flight response and since this is an internally generated sound one can not control its volume or remove themselves from it.

In the case of tinnitus, once the new pattern of auditory neural activity is detected and locked into the limbic system the tinnitus becomes extremely prominent. Basic neuroscience predicts that it is relatively easy to reverse this signal recognition process by exposing the patient to low levels of broad band noise for a long period of time. This broad band noise will interfere with the tinnitus recognition process making it more difficult to separate the tinnitus signal from background neuronal activities and, since there are no longer other processes increasing recognition of this intruding signal the tinnitus becomes no longer detected.

In recent years masking of tinnitus using various noise signals of adjustable width and amplitude have been developed as a result of scientific research done by Jack Vernon. These devices yielded very limited success. More recently, a neurophysiological model of tinnitus management has been developed by Pawel Jastreboff. Using specific protocol, attempts were made to habituate patients to the presence of tinnitus. Habituation infers training patients not to be aware of tinnitus except when deliberately focusing their attention on it. Even then, perceived tinnitus should no longer induce annoyance or irritation.

It has been shown that the introduction of a noise signal can help in the therapy. Behind-the-ear noise generators have yielded an 83 percent success rate. Yet the units remain big, cumbersome and cosmetically unappealing.

Manufacturers of hearing aids are regulated by the United States Food and Drug Administration (FDA) as a medical device establishment. Hearing aid components used in the assembly of custom open-ear tinnitus habituators and produced as a combined hearing aid/tinnitus habituator device or as a stand-alone tinnitus device will be categorized, not as a Class I hearing device, but rather as a Class III prosthetic device under 21 C.F.R. § 874.3400 entitled "Tinnitus masker". The tinnitus habituator differs from the tinnitus masker in that it does not emit a signal intended to overpower the tinnitus head/ear noise, but to stimulate the auditory pathways with a broad-band low-level signal. Its intent, however, is to aid in tinnitus and FDA has decided the device described in this application will fall into the Class III classification. FDA regulates medical devices based on safety and effectiveness. The hearing aid components used in the construction of the tinnitus habituator have been used in the assembly of millions of Class I hearing aids and are therefore known to be safe when used as directed. The efficacy is the issue, in that there is no established protocol by FDA in the management of tinnitus. The Class III classification stems from the absence of this protocol. The Class I level would be more cost-efficient to produce and in turn reduce the cost to the public. It is the protocol that teaches the patient to focus on the signal of the tinnitus habituator and not focus on the tinnitus head noise which enables the tinnitus device though central auditory habituation to reduce the debilitating effects of tinnitus or hyperacusis. Tinnitus habituators without a well designed therapy would not be significantly effective. Also, masking tinnitus via a traditional masker is counter productive (Gold S. L., Gray W. C., Hu S., and Jastreboff P. W. "Selection and Fitting of Noise Generators and Hearing Aids for Tinnitus Patients", *Proceedings of the Fifth International Tinnitus Seminar* 1995 edited by Reich G. E. and Vernon J. A. ©American Tinnitus Association, Portland Oreg. U.S.A. 1996 p.312–314; Jastreboff P. J. and Hazel J. W. P. "A Neurophysiological Approach to Tinnitus: Clinical Implications" *British Journal of Audiology,* 1993. 27. 7–17). It is very important to avoid masking tinnitus. In fact, there are reports of patients having long term "masking" therapy who realized no relief from the perception of the tinnitus or the annoyance resulting from the tinnitus. After entering into habituation therapy, both the perception of and the annoyance from tinnitus were reduced (Jastreboff P. J., Gray W. C., and Gold S. L.: "Neurophysiological Approach to Tinnitus Patients", *The American Journal of Otology,* 17:236–340 ©1996).

Products designed to be used to fill the room with a low level noise, not FDA regulated, have proven to offer minimum effectiveness, because sound reaching the ear drum is unstable and inconsistent due to head shadow effect, occlusion to the external ear canal, and the Doppler effect caused by motion of the patient's head, such as turning back and forth vigorously. Additionally, the size of this unit makes it difficult to transport and impractical to use outside of the home since the noise would distract others.

U.S. Pat. No. 5,403,262 issued to Gooch describes a circuit means of random noise generation, which is digitally processed to selected center frequencies, bandwidth and intensity. A random noise signal is transduced to acoustical energy by a speaker or headphone. Other means of delivering the masking signal to the patient's ear may be by way of using a low-power transmitter or electromagnetic coil to deliver the signal from the tinnitus masker to a receiver worn in or on the sufferer's ear. Gooch's circuit is intended for room noise generation to mask tinnitus, not habituate it, as a patient goes to sleep.

U.S. Pat. No. 5,325,872, issued to Westerham et al., discloses an invention which relates to a Tinnitus masker with one or more signal generators, a controllable amplifier, transducers and comprises means for generating a continuously repeated, sinusoidal pure-tone signal which continuously and slowly moves through an audiofrequency range in a cyclic manner to remove tinnitus for a period of time. Westerham et al. predicates its design of the masker on the reasoning that "tinnitus is very frequently perceived as a tone". The described embodiment is a behind-the-ear (B-T-E) device.

U.S. Pat. No. 4,222,393 issued to Hocks et al. describes a Tinnitus masker device whereby the patient is subjected to external sounds of different pitch, one right after another, to enable the patient to identify the particular external sound having the same pitch as the subjective tinnitus sound perceived by the patient. The patient is then provided a power-operated sound generator producing a range of frequencies extending above and below the perceived pitch to mask the tinnitus sound. The tinnitus masker may be worn in the same manner as a hearing aid or combined with one. Once again, the device is a masker intended to immerse the tinnitus head noise below audibility. This is accomplished by using a noise signal with a patient-selected center frequency where the output noise signal is of broader band-width and intensity than the tinnitus therefore facilitating a masking effect of the tinnitus. The actual noise generation of the masker is by a noise generator. It can only be produced in a behind-the-ear instrument.

U.S. Pat. No. 5,167,236 issued to Junker describes a behind-the-ear Tinnitus-masker which is an electronic circuit designed so that the sound spectrum produced through an ear-piece contains a line spectrum with a fundamental tone.

U.S. Pat. No. 4,870,688 issued to Voroba et al. describes a hearing aid comprising an electronic circuit designed using a pseudorandom frequency noise generator as a sound source to be connected to a hearing aid circuit for use in patients with "ringing" or "buzzing" in the head, commonly called tinnitus. The drawings in the patent do not define the object and only identify a standard hearing aid microphone as the source.

Other patents that may be of interest include the following:

U.S. Pat. No. 5,024,612, External ear canal pressure regulating device and tinnitus suppression device;

U.S. Pat. No. 5,628,330, Apparatus for treating people afflicted with tinnitus;

U.S. Pat. No. 4,735,968, Method of treating tinnitus with AOAA;

U.S. Pat. No. 5,279,292, Charging system for implantable hearing aids and tinnitus maskers;

U.S. Pat. No. 5,064,858, Protected complex of procaine for the treatment of symptoms from narcotics addiction, tinnitus and Alzheimer's disease;

U.S. Pat. No. 4,954,486, Furosemide as tinnitus suppressant;

U.S. Pat. No. 4,984,579, Apparatus for treatment of sensorineural hearing loss, vertigo, tinnitus and aural fullness;

U.S. Pat. No. 4,956,391, Protected complex of procaine for the treatment of symptoms from narcotics addiction, tinnitus and Alzheimer's disease;

U.S. Pat. No. 5,589,183, Method and apparatus for treatment of neurogenic diabetes mellitus, and other conditions;

U.S. Pat. No. 4,759,070, Patient controlled master hearing aid;

U.S. Pat. No. 4,226,248, Phonocephalographic device;

U.S. Pat. No. 5,563,140, Use of 1-(aminoalkyl)-3-(benzyl)-quinoxaline-2-one derivatives for the preparation of neuroprotective compositions;

U.S. Pat. No. 4,680,798, Audio signal processing circuit for use in a hearing aid and method for operating same;

U.S. Pat. No. 3,764,748, Implanted hearing aids;

Whether the failure of current tinnitus devices is due to the incomplete or inaccurate clinical knowledge or whether the failure is existing product performance, the end result is tinnitus and hyperacusis patients are experiencing an inadequate quality of life.

All patents mentioned herein are incorporated herein by reference.

BRIEF SUMMARY OF THE INVENTION

The apparatus of the present invention solves the problems confronted in the art in a simple and straightforward manner.

Unlike Gooch, the present invention is completely self-contained in the ear shell and does not use electromagnetic or transmitter technology. Further, it does not incorporate digital technology for band-width and center-frequency selection. The present invention performs optimally in open-ear design. In many cases the stimulator can be combined with a hearing aid circuit to compensate for a hearing loss.

Unlike Hocks et al., the present invention embodies an open-ear in-the-canal device without insertion loss and with better cosmetics. Further, noise generation is by thermal circuit noise, requiring fewer electronic components and better product reliability.

Unlike Voroba et al., the sound source in the present invention is a thermal noise specifically designed for band width, gain and low current drain optimized for hearing aid batteries. It is not a pseudorandom frequency noise generator.

The present invention provides sound of stable temporal characteristics, such that head movement does not cause a change in the signal at the TM of the wearer of the present invention.

The present invention provides a wide band sound spectrum to emulate real world sound so there is not a strong negative association with a new pattern sound in the central auditory system.

The present invention is a cosmetically superior design as compared to a BTE with the earmold and connecting tube assembly. This feature is genuinely beneficial since the perception of tinnitus sound or any sound can be habituated only when the stigma of wearing the device does not evoke any form of negative emotional response.

The present invention allows enhanced telephone use with the product of the present invention in place.

The current invention does not have moisture problems as those associated with BTE's in the earmold tubing; the current invention eliminates the need for earmold tubing.

The current invention has a matched acoustic response for both ears since the earmold and earmold tubing are eliminated.

The current design yields a better angle of attack for the sound spectrum to impinge the TM as compared to the BTE whose receiver is housed behind the ear and must travel through earmold tubing and the earmold. Variances in the tubing length and earmold insertion depth of BTE's affect the spectrum greatly.

The current invention is less susceptible to wax impaction since the receiver is located in the superior external ear canal quadrant.

The present invention has a volume control taper which allows very discrete adjustment of low level sounds while maintaining a very stable signal output.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

During development, as the open ear auditory pathway stimulator, to manage tinnitus and hyperacusis, was nearing completion, it was referred to as a Tinnitus Retraining Instrument (TRI). This describes the associated therapy more than the device but segregates it from other devices, such as maskers.

Figure 1:
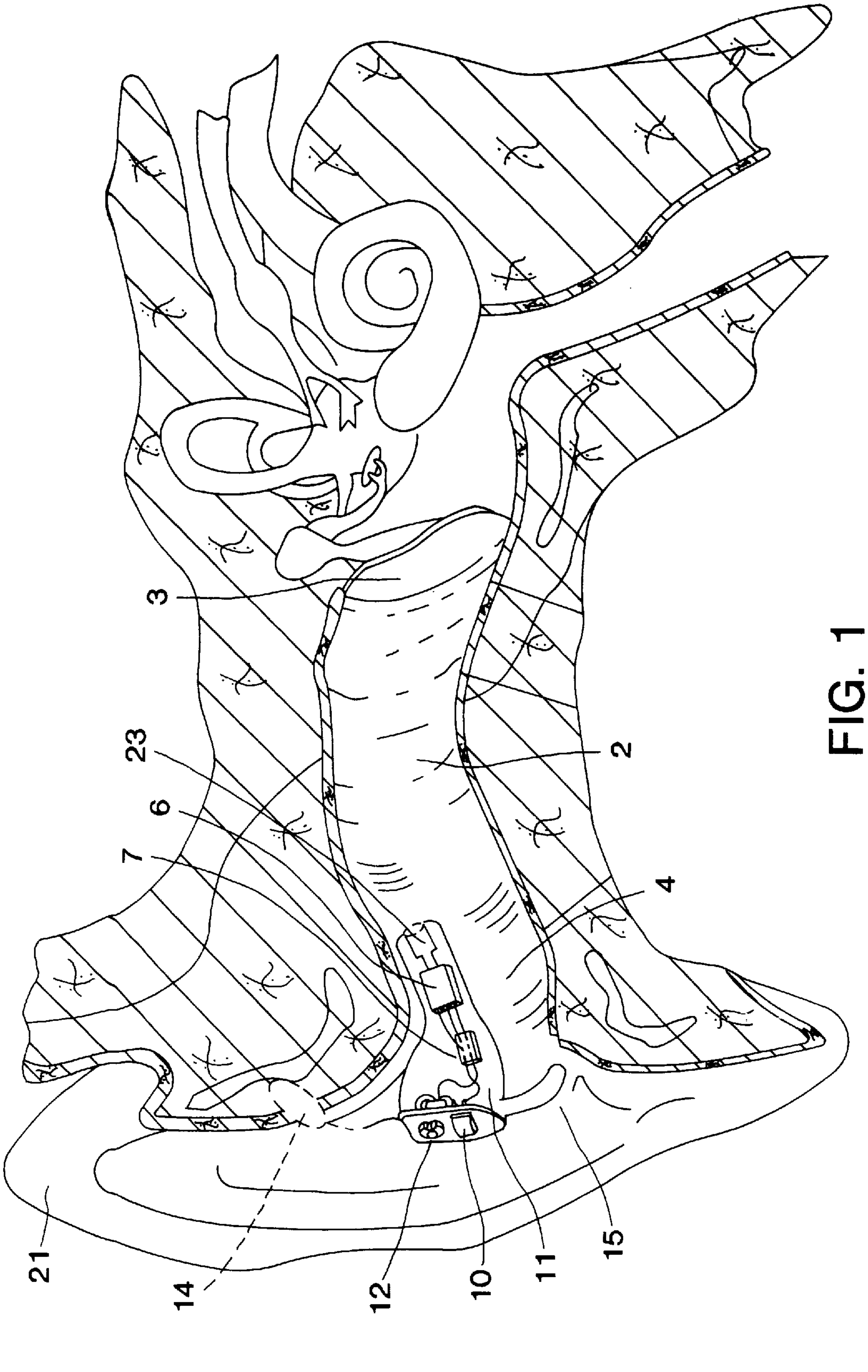
FIG. 1 shows a canal open-ear device in a human ear.

FIG. 1 shows one configuration of a complete TRI device 1 in the human ear from a side perspective. FIG. 1 shows a canal open-ear model 1 made in an acrylic shell. The tympanic membrane, TM, or ear drum 3 is deflected by sound waves emitting from the receiver 6 of the TRI 1. Two sources of sound reach the TM 3. One, sound is delivered by the TRI. The other sounds arrive from surrounding ambient sources, such as another human voice. The construction of the TRI 1 is such that the external ear canal 2 is completely open in the inferior portion or bottom half 4. This is important to assure delivery of normal outside sounds, without introducing intermodulation that would alter the original signal. If the external ear canal is occluded, typically low frequencies are introduced, making the wearer report that their voice sounds like it is in a barrel. If the external ear canal 2 is sufficiently open (approximately 50 percent), the ear canal resonance is unchanged and the wearer reports normal sound quality. The same performance would be accomplished if the superior ear canal were left open, although wax-related problems with the receiver 6 make it a less-than-optimum design in terms of product reliability. The retention arms 14 and 15 position the shell housing of the TRI 1 to maintain the openness of the external ear canal 2 and properly aim the receiver at the superior portion of the TM 3, its most sensitive surface area. The electronic circuit is mounted on the faceplate 9 (see FIG. 3) with a battery door 10 and battery contacts 11 connecting power via litz wire 13 to the noise source 8 then to the amplifier 7 and on to the receiver 6, where noise is generated and directed through an acoustic horn 23 to the TM 3. The level of transmitted noise is adjusted by the volume control 12. The canal-open-ear (COE) design is cosmetically a superior design as compared to a behind-the-ear (BTE) with the earmold and tubing connection which fits over the external ear (pina) 21. This is genuinely beneficial, since the perception of tinnitus sound can be habituated only when the stigma of wearing the device does not evoke any form of an emotional response associated with wearing the device.

One could use a Microtronic #6 volume control adapter ring and wire 13 could be insulated stranded wire similar to Litz 44 gauge 5 strand magnet wire.

With the present invention, there is enhanced telephone use with the product in place, in terms of sound transmission and the placement of a phone receiver adjacent the external ear canal, as in usual use. The BTE product must be repositioned with the telephone receiver if the BTE is also a hearing aid or removed if the BTE is not equipped with a microphone. Additionally, the present invention has a matched acoustic response for both ears since the earmold and earmold tubing associated with BTE's are eliminated. The current design yields a better angle of attack for the sound spectrum to impinge the TM 3 as compared to the BTE whose receiver is housed behind the ear and must travel through earmold tubing and the earmold. Variances in the tubing length and earmold insertion depth affect the spectrum greatly. The present invention has a sound envelope of stable temporal characteristics, where head movement will not cause a change in the signal at the TM 3.

Figure 2:
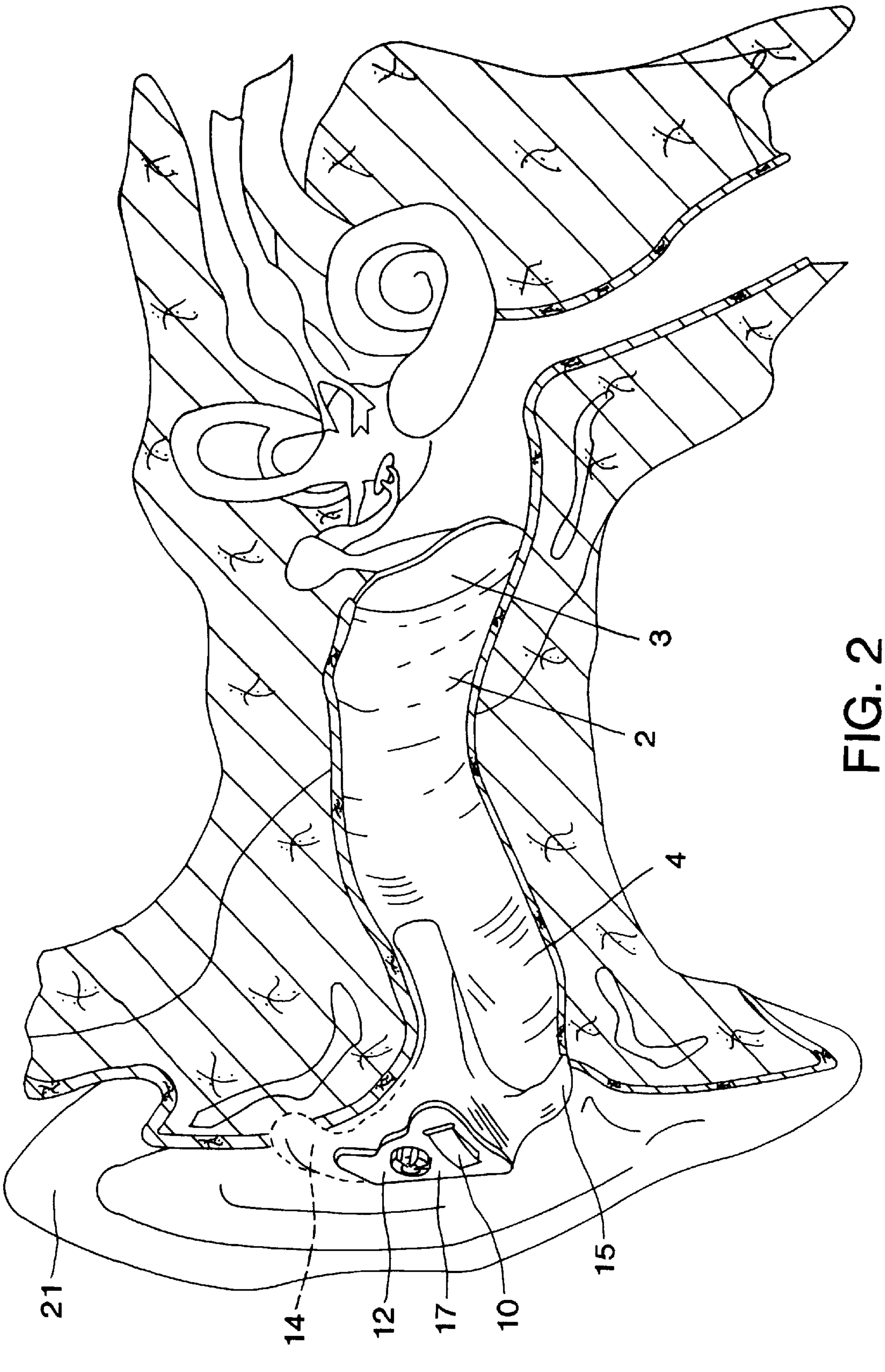
FIG. 2 shows a Helix open-ear device in a human ear.

FIG. 2 shows an open ear, helix based TRI 17. It is used to fit ears which are too small for the COE or CIC units by filling the concha bowl in the helix of the pina 21. The theory of operation is as above. A larger battery can also be used, increasing service life between battery changes.

Figure 3:
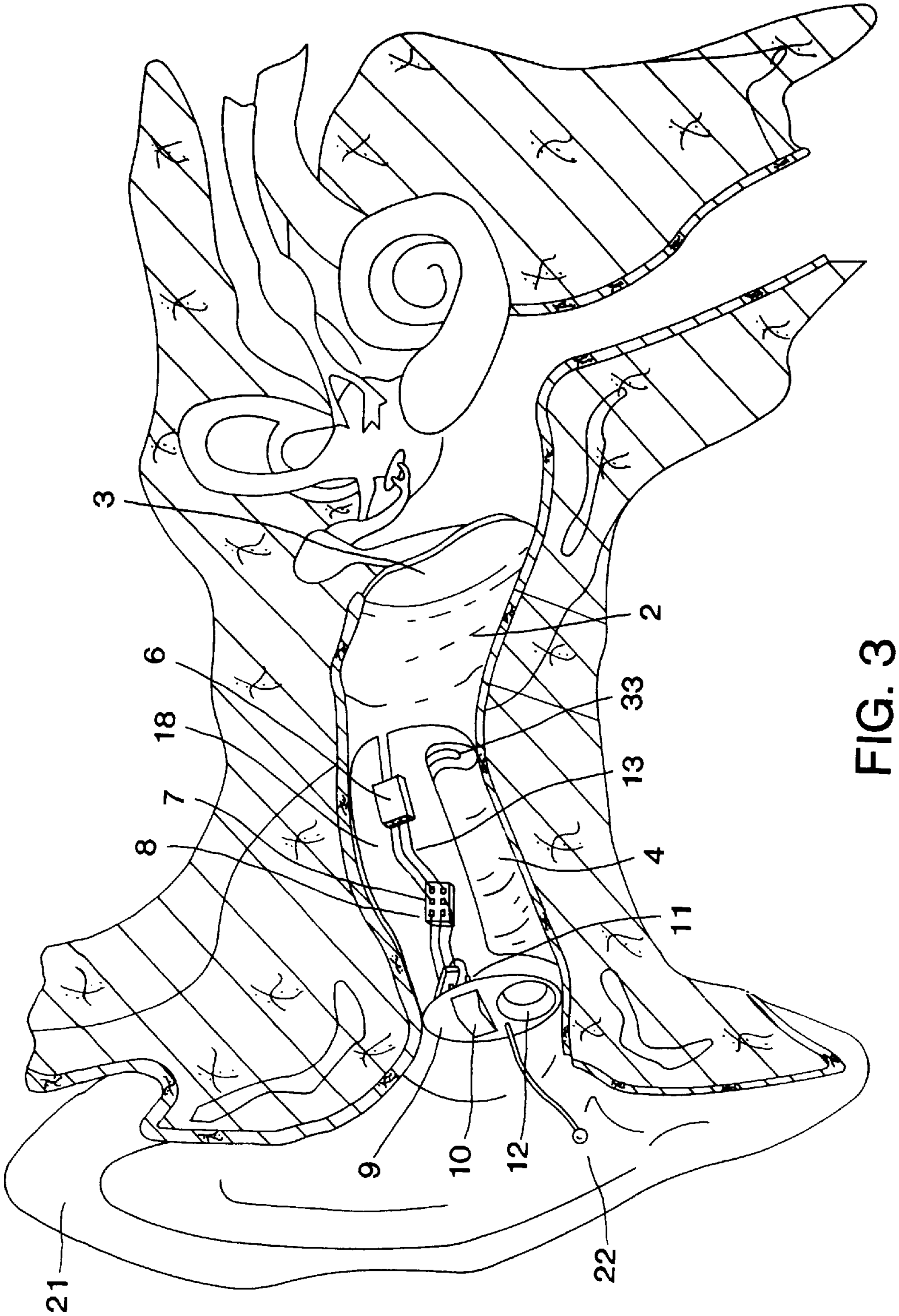
FIG. 3 shows a CIC open-ear device in a human ear.

FIG. 3 shows an open ear, completely-in-the-canal (CIC) based TRI 18. The CIC TRI 18 uses a unique positioning system to properly aim the receiver 6 at the TM 3. As in FIG. 1, this positioning is important to deliver a sound envelope of stable temporal characteristics, where head movement will not cause a change in the signal at the TM 3. The sagital plane or face plate 9 is designed to have an opening at the apex of the external ear canal 2, then to leave the inferior portion 4 of the ear canal free and unobstructed medially until the distal, or medial end of the device where a medial ipsolateral-route-of-signal (IROS) vent retainer 33 supports the device 18 upward into the superior portion of the external ear canal 2 and at the same time keeping the inferior canal 4 open and veritably unobstructed for free-field sound transmission. The CIC is the product of choice to offer the best cosmetic solution and has a built in extraction cord 22 since the device resides deeply in the external ear canal 2. This extraction cord 22 also serves as a volume control extension which allows adjustment of the noise level by rolling the nubbin on the cord between the index finger and thumb. The CIC design preferably uses a battery size "5 A" and should use an efficient circuit, such as the class D (FIG. 8 ), to have a reasonable battery life.

Figure 4:
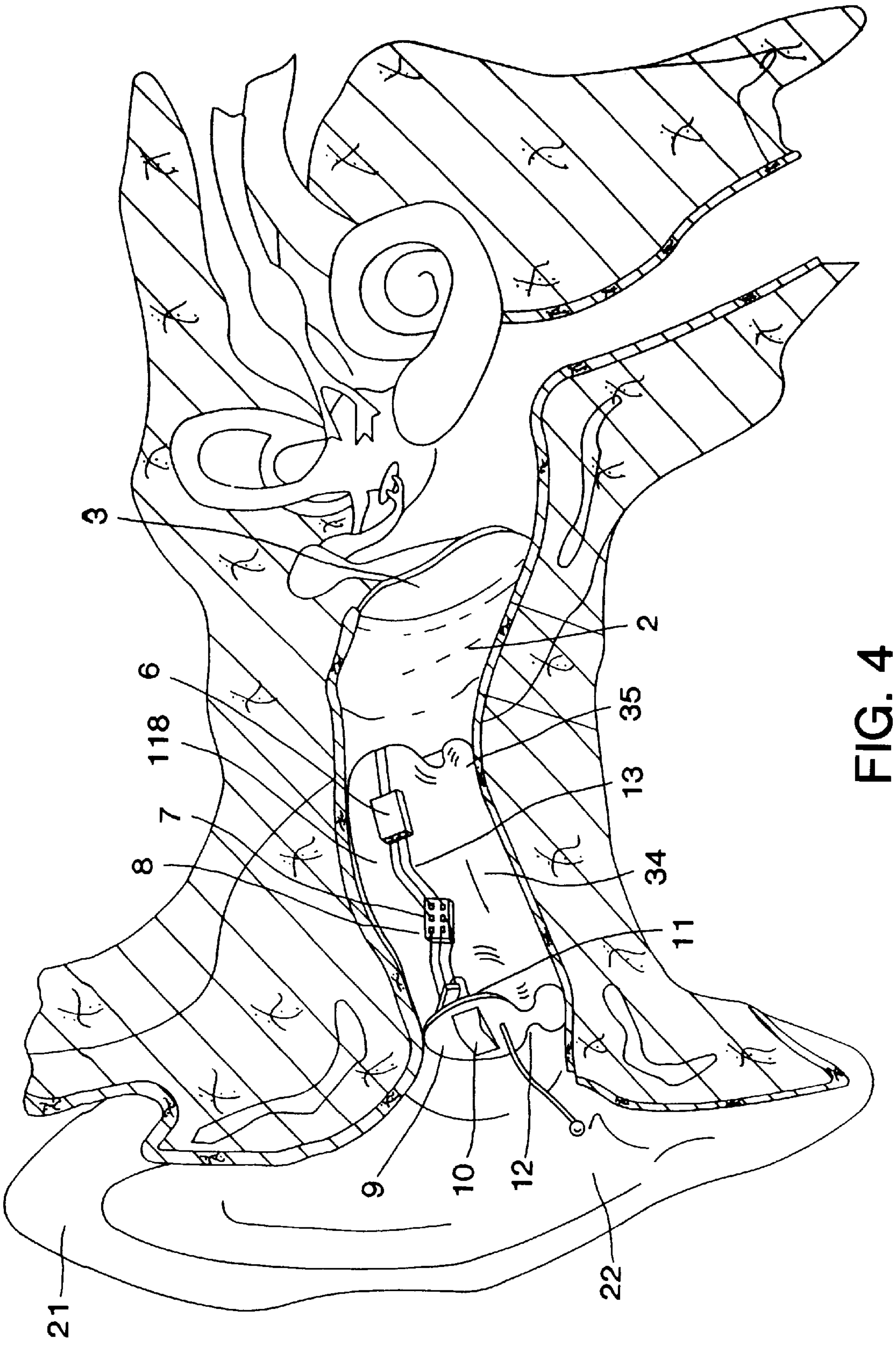
FIG. 4 shows the CIC open-ear device with an alternative retention system to hold the device in place in the human ear.

FIG. 4 shows an alternative retention design for an open ear CIC 118; all theory of operation remains the same.

Figure 5:
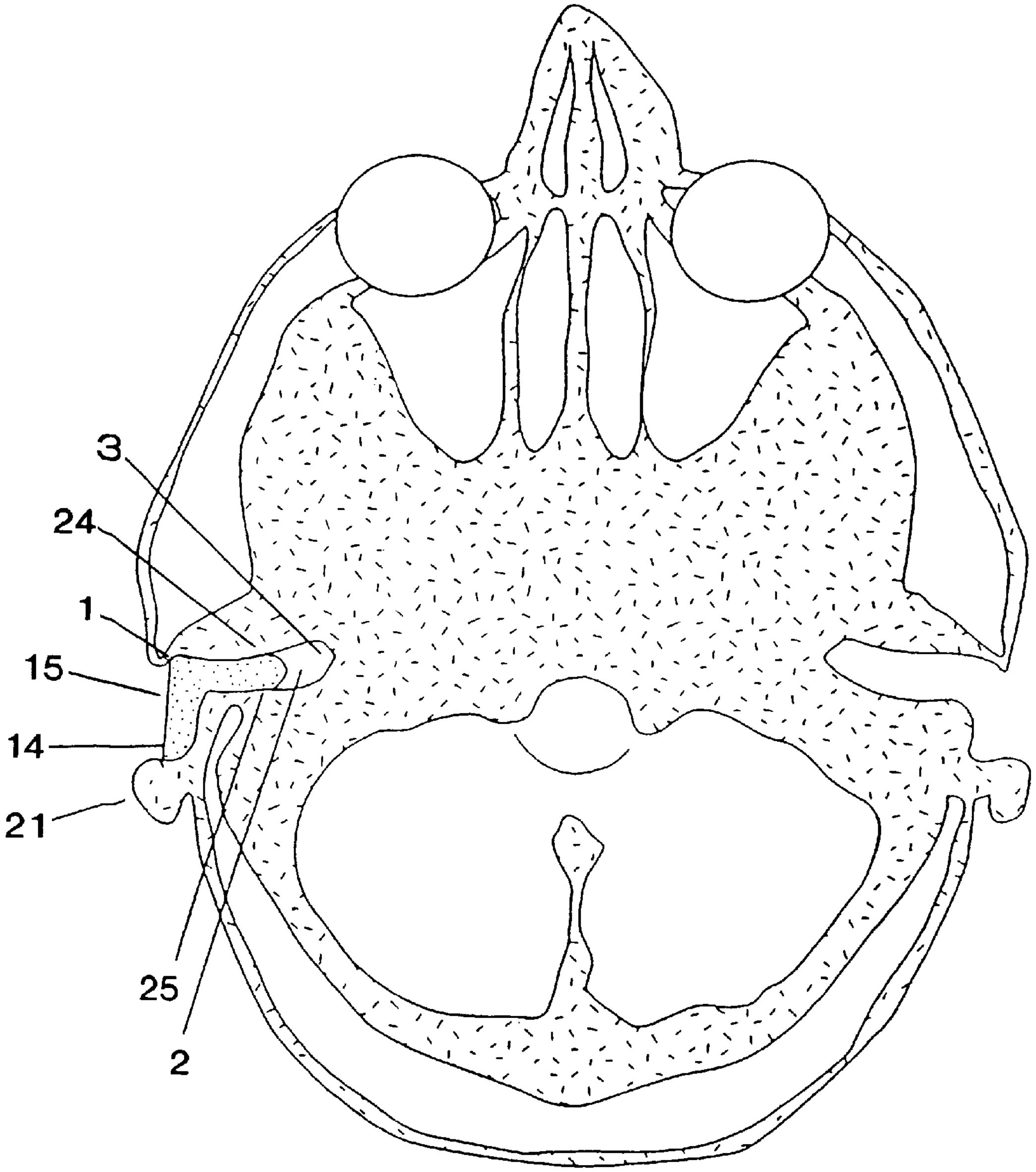
FIG. 5 shows the device graphically illustrated via magnetic resonance imaging (MRI) in a typical human ear as viewed from the top of the head, superior to inferior.

FIG. 5 shows a COE based TRI device graphically illustrated via magnetic resonance imaging (MRI) in a typical human ear as viewed from the top of the head, superior to inferior. The external ear canal 2 and its first and second directional bend are exhibited. The anterior 24 and posterior 25 planes are shown to demonstrate how the COE shell must be molded to faithfully follow the ear canal. The helix 14 and cavum 15 retention arms maintain the spatial relationships to fill the superior canal while the inferior canal 4 is left open, at the same time the anterior 24 and posterior 25 canal quadrants are filled, aiming the receiver at the superior portion of the TM 3.

Figure 6:
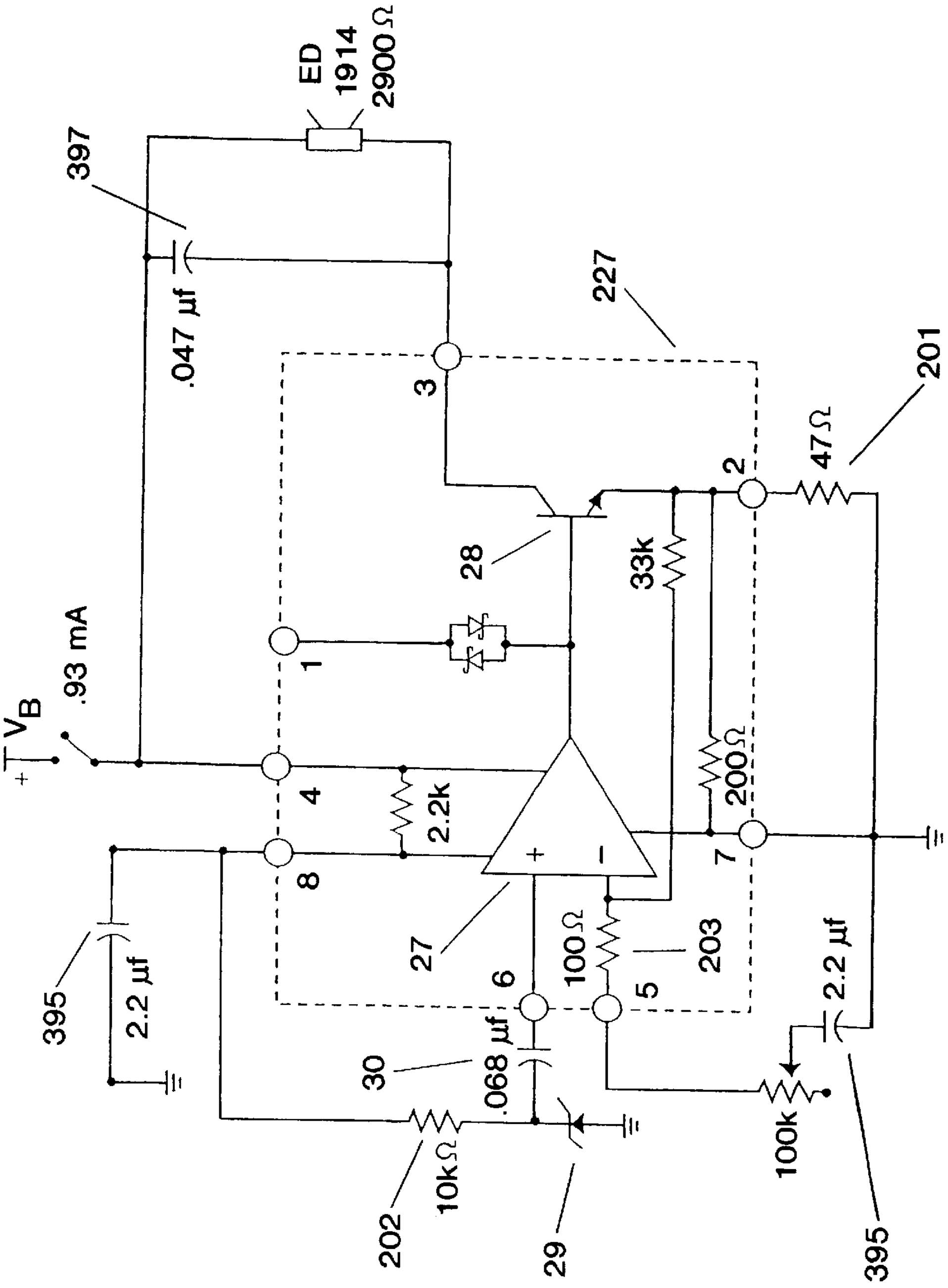
FIG. 6 shows a preferred embodiment of a Class A electrical circuit, in which the volume control is accomplished with a 100K ohm variable resistor in which minimum resistance yields maximum volume.

FIG. 6 shows a preferred embodiment of a Class A electrical circuit. A basic operational amplifier 27 feeds into a transistor 28 forming the basic circuit. A Zener diode 29, Motorola type MLL4684 or equivalent, is set between ground potential and input into a capacitor 30 which establishes the corner frequency of the amplifier circuit. The noise generator formed by the Zener diode 29 and the RC input circuit requires very little current drain which is primarily dictated by the requirements of the OpAmp/Transistor. The transducers are selected based on frequency response and impedance. Higher impedance transducers reduce the current draw. The total current drain required for the device is governed by the electrical/acoustic efficiency of the transducer and how much sound volume the device is set to deliver. The volume control 12 taper is selected to have as much "bend" in it as possible. The reason is that most of the control occurs in the first few thousands of Ohms of resistance. So if the resistance selected on the volume control is minimum, gain is maximized to the loudest noise output. Resistance taper of the volume control yields about one and a half dB increments with a range typically of twenty-four dB. In FIG. 6, the transducer is a model ED 1914 commercially available from Knowles Electronics, Chicago, Ill., and $V_B$ is a battery which can last typically about 60 hours.

Figure 7:
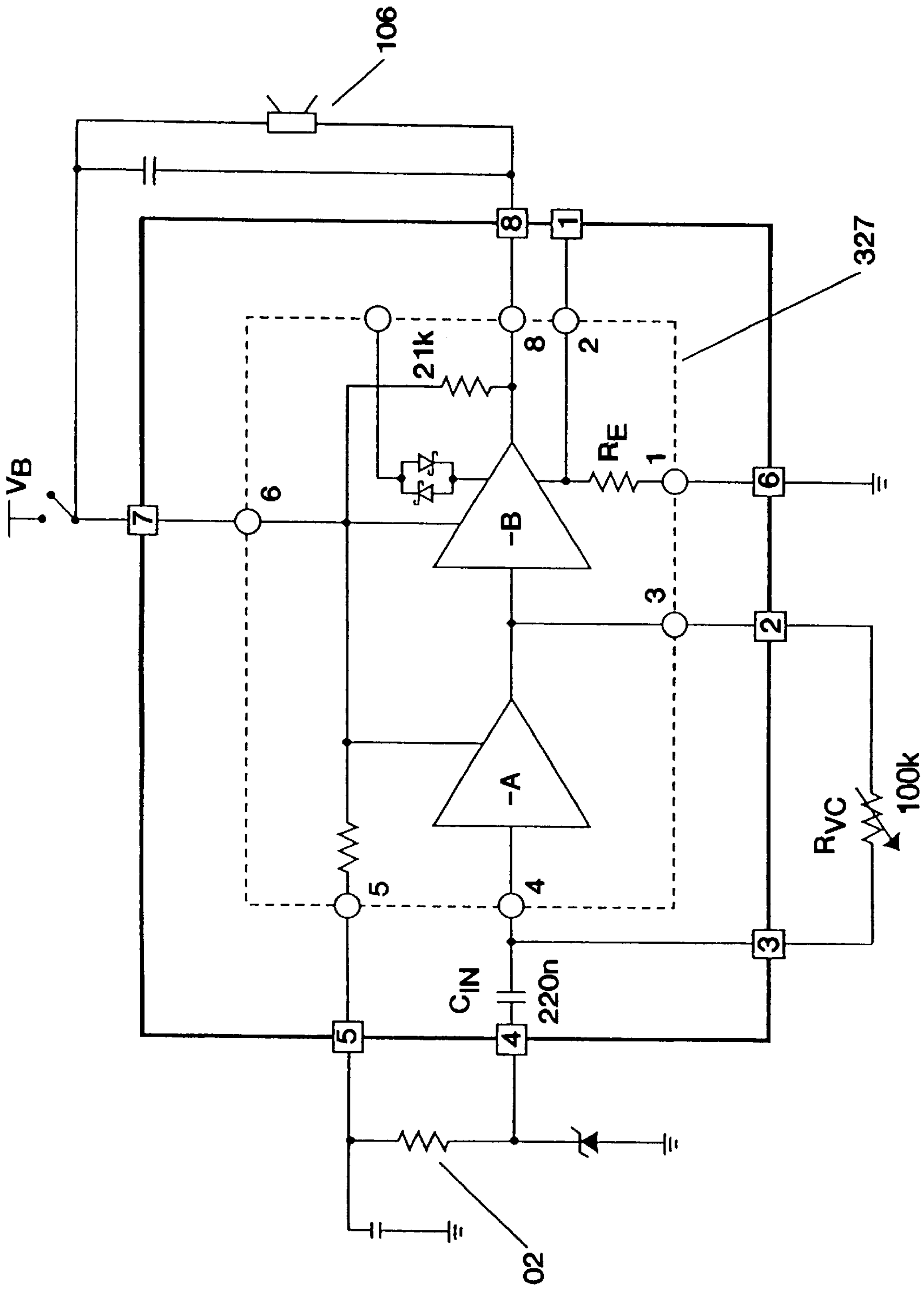
FIG. 7 shows a preferred embodiment of a two-stage Class A electrical circuit.

FIG. 7 shows a preferred embodiment of a two-stage Class A electrical circuit which has balanced stages for smoother voltage gain resulting in improved stability of signal and better battery life.

Figure 8:
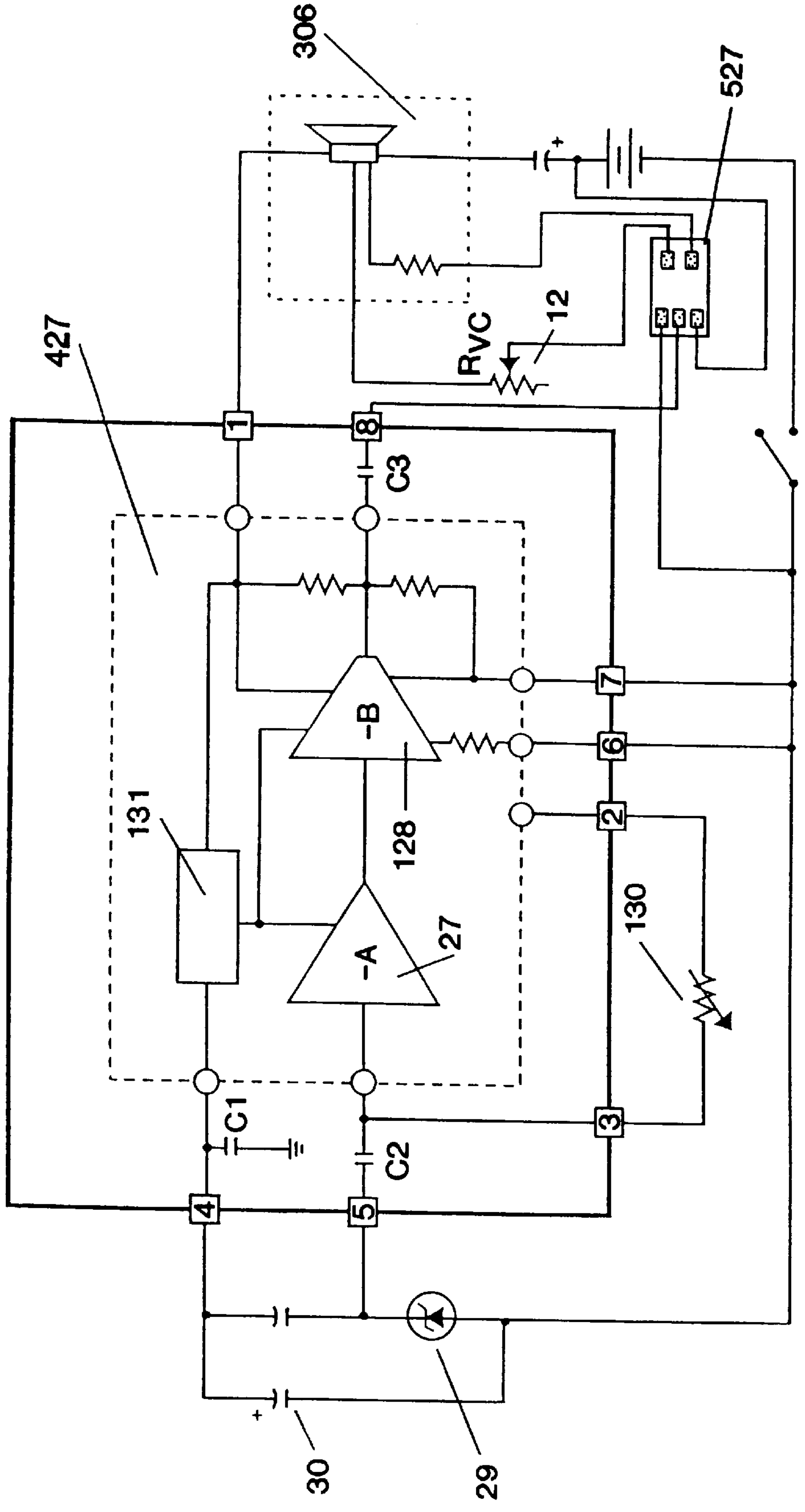
FIG. 8 shows a preferred embodiment of a three-stage Class D electrical circuit.

FIG. 8 shows a preferred embodiment of a three-stage Class D electrical circuit device combined with any of the shell models described herein or manufactured with an application-specific integrated circuit, where the amplifier input stage and the C-MOS output stage (class D) are populated on the same hybrid or on two separate hybrids. A basic operational amplifier 27 feeds into an inverting operational amplifier 128 forming the basic circuit. A Zener diode 29, Motorola type MLL4684 or equivalent, is set between ground potential and input into a capacitor 30 which establishes the corner frequency of the amplifier circuit. The noise generator formed by the Zener diode 29 and the RC input circuit requires very little current drain which is primarily dictated by the requirements of the Op Amp/Inverting Op Amp. The transducers are selected based on frequency response and impedance. Higher impedance transducers reduce the current draw. The total current drain required for the device is governed by the electrical/acoustic efficiency of the transducer and how much sound volume the device is set to deliver. The volume control 12 taper, as in the Class A design, is selected to have as much "bend" in it as possible. The reason is that most of the control occurs in the first few thousands of Ohms of resistance. The gain of the circuit is determined by a sum of the series gains of the subcircuits measured in decibels. So if the resistance selected on the volume control is minimum, gain is maximized to the loudest noise output. Resistance taper of the volume control yields about one and a half dB increments with a range typically of thirty-eight dB. In FIG. 8, the receiver 306 could be a model FD 3286 or model FD 3287, commercially available from Cherry Electronics, Chicago, Ill. Trimmer 130 is a 100K variable resistor.

Figure 9:
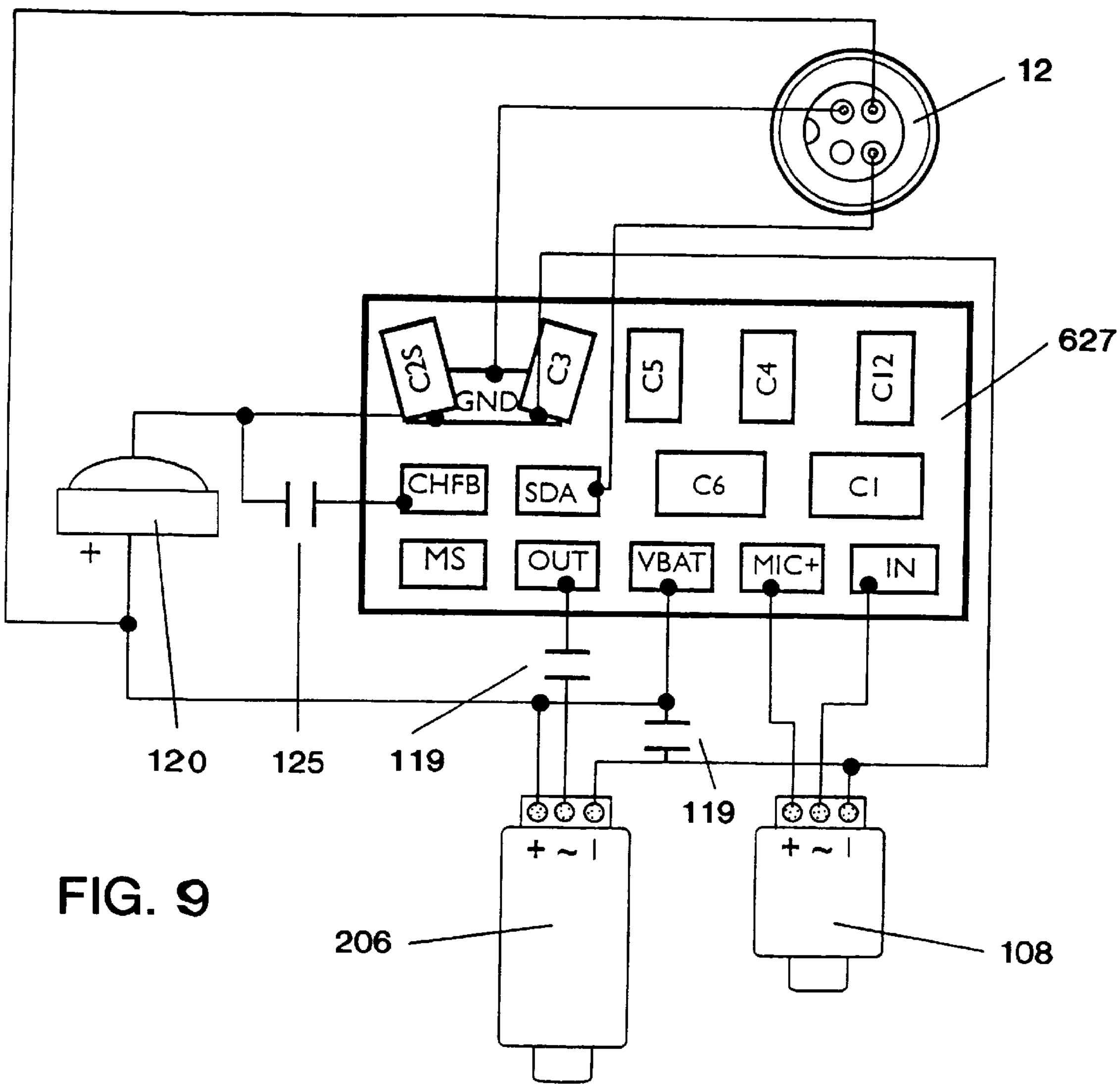
FIG. 9 shows a preferred embodiment of a programmable K-amp three-stage Class D electrical circuit.

FIG. 9 shows a preferred embodiment of a programmable K-amp three-stage Class D electrical circuit. A suitable circuit for this purpose is shown in U.S. Pat. No. 5,131,046.

Figure 10:
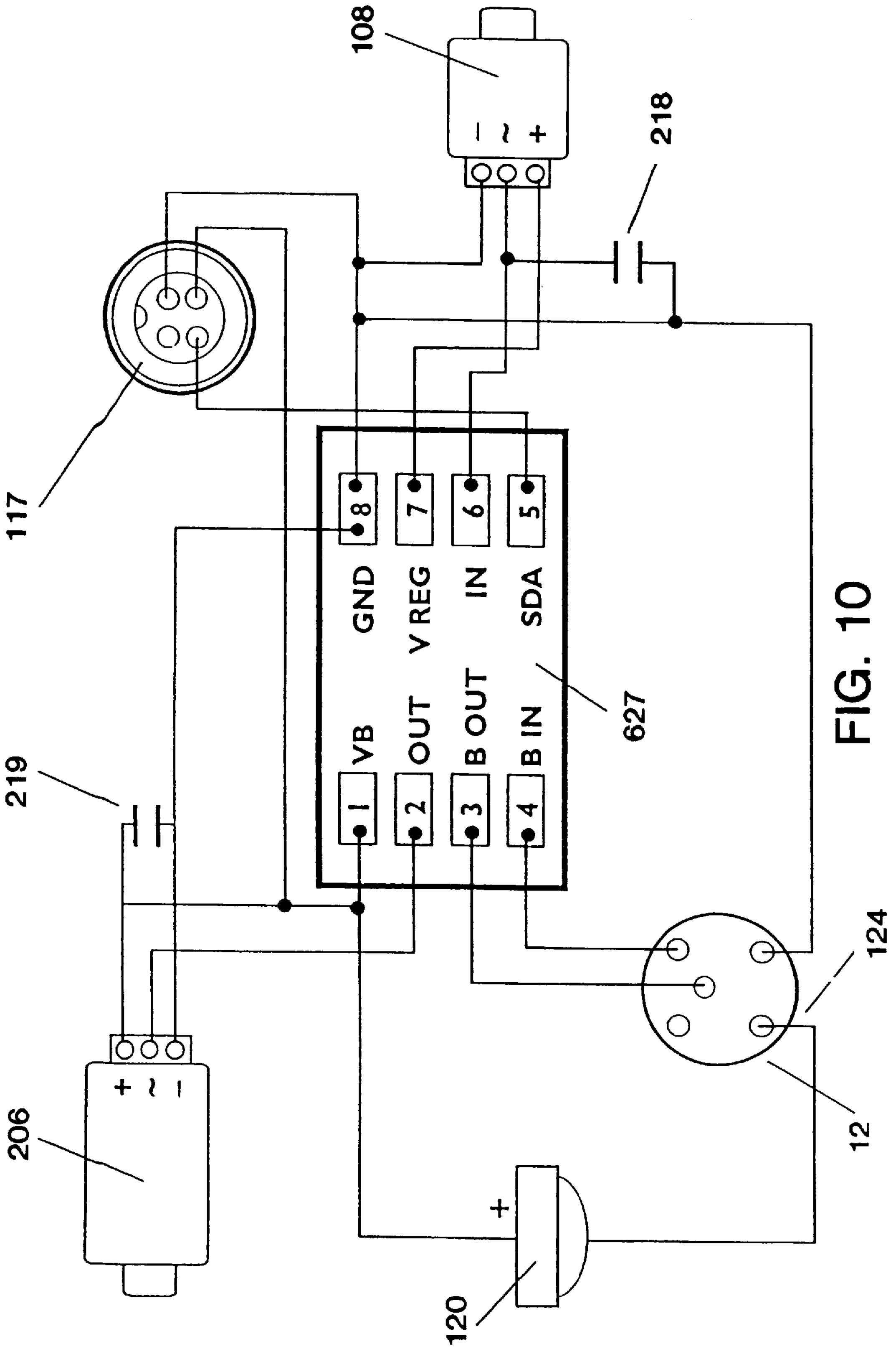
FIG. 10 shows a preferred embodiment of a programmable Intrigue™ three-stage Class D electrical circuit.

FIG. 10 shows a preferred embodiment of a programmable Intrigue™ three-stage, two-channel Class D electrical circuit.

Figure 11:
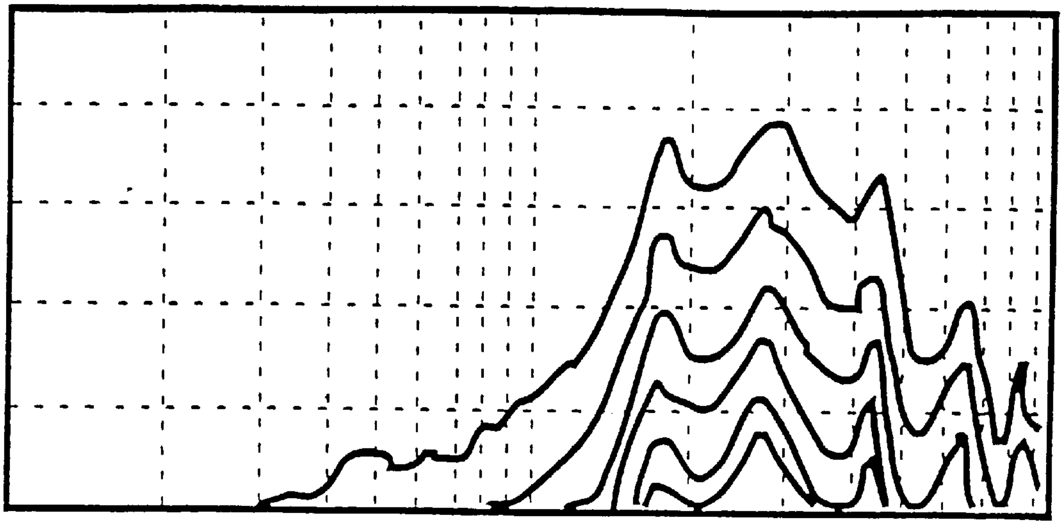
FIG. 11 shows the frequency response of various volume control positions of the TRI.
Figure 12A:
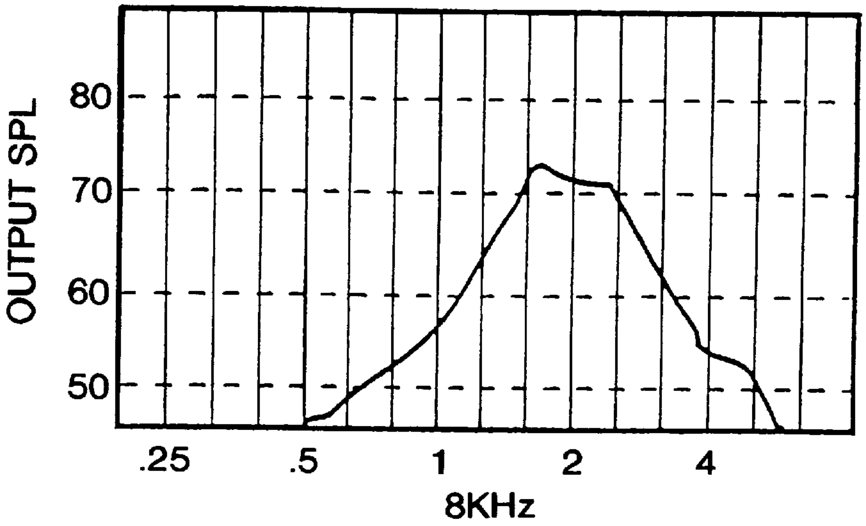
FIGS. 12A–12E show frequency spectrums of the noise signal with a 1.5V battery, wherein "SPL" is root-mean-square noise sound pressure level generated by the device of the present invention, with FIG. 12A showing a maximum level of 82.1 dB SPL, with FIG. 12B showing a maximum level of 82.7 dB SPL, with FIG. 12C showing a maximum level of 82.9 dB SPL, with FIG. 12D showing a maximum level of 85.5 dB SPL, with FIG. 12E showing a maximum level of 86.4 dB SPL.
Figure 12B:
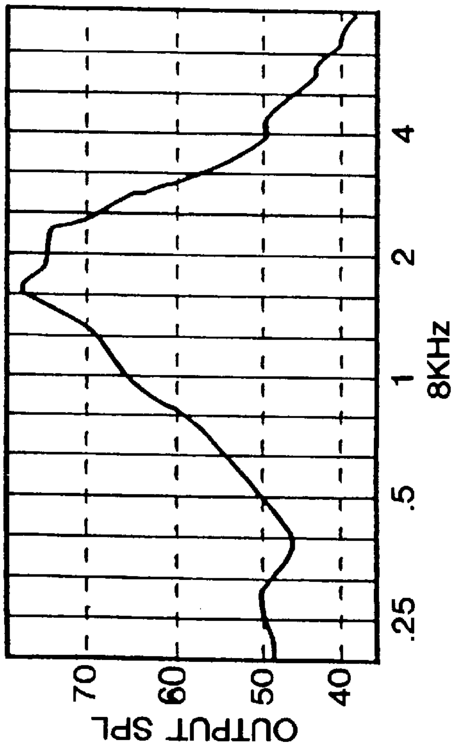
Figure 12C:
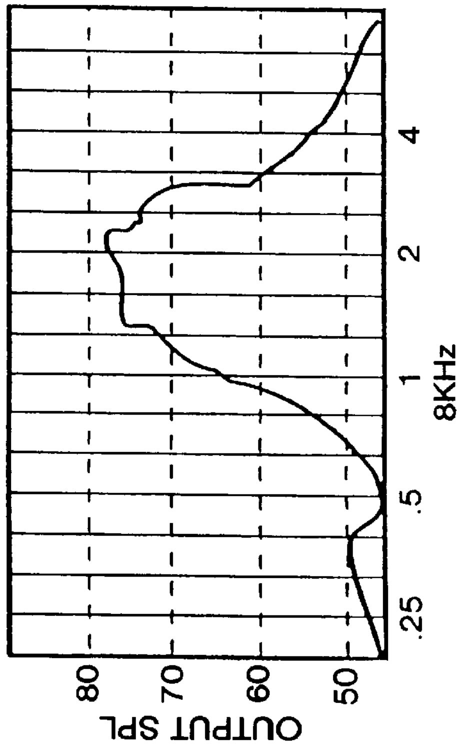
Figure 12D:
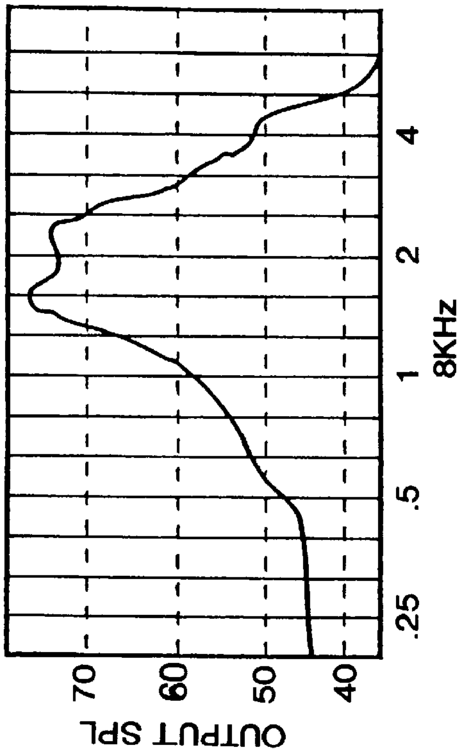
Figure 12E:
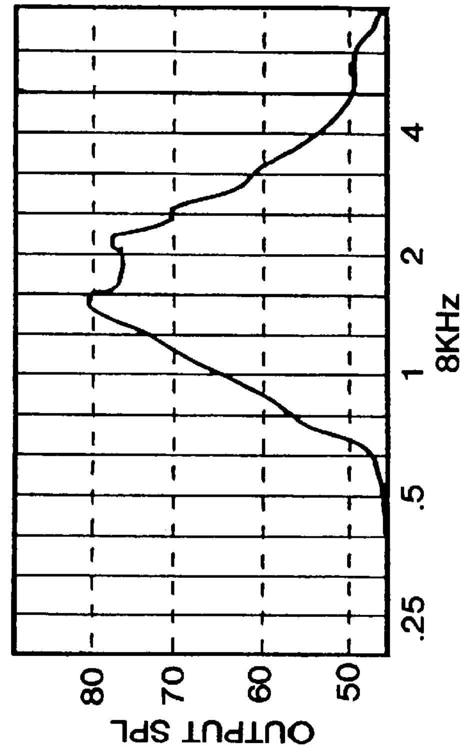

FIG. 11 shows the frequency response of various volume control positions of the TRI 1, as measured on a Madsen Electronics, Inc. Model "Auricle" using a NOAH interface with a direct access 2 cc coupler. Table 1. shows the relationship of volume control rotation to noise gain. The taper of the volume control (VC) is set to give very discrete adjustment in the very low gain, barely audible ranges, with excellent voltage stability and a sound envelope of stable temporal characteristics, where head movement will not cause a change in the signal as measured at the TM 3. The VC was further designed to have a very quiet operation, free of scratchiness and changes in the consistency of taper during increase or decrease of gain.

FIGS. 12A–12E show the spectrum characteristics of the intact noise stimulator which generates between an 82 dB and 85 dB noise level. The data is the average for nine devices.

PARTS LIST

The following is a list of elements used in the drawings and potential commercially available products which could be used as these elements:

1 COE shell
2 external ear canal
3 TM
4 inferior quadrant of the external ear canal
6 receiver
7 amplifier circuit
8 noise source circuit
9 face plate (such as an Entech 10A face plate)
10 battery door (such as an Entech 10A battery door)
11 battery compartment (e.g., an Entech 10A insulated battery compartment boot)
12 volume control (Microtronic, e.g.)
13 litz wires
14 concha retention arm
15 cavum retention arm
17 Helix Based OE-TRI device
18 CIC based TRI device
21 pina
22 extraction cord
23 acoustic horn
24 anterior ear canal
25 posterior ear canal
27 operational amplifier
28 transistor
29 Zener diode (such as a NTE Electronics Cat # 5005A Zener Diode)
30 capacitor (such as a Tansitor® 0.068 microfarad capacitor)
33 vent retainer
34 vertical wall occupying coronal plane from superior to inferior to keep device 118 in place despite jaw action
35 footer to spread pressure of downward force of device 118 onto the inferior external canal across a sufficient surface area so as not to cause undue pressure on the superficial nerve endings of the external ear canal
106 Knowles® ED 1914 receiver
108 Microphone (Knowles)
117 Microtronic variable resistor
118 alternative CIC based TRI device
119 output capacitor (Tansitor®)
120 1.1 V DC battery cell (typically #13, 312, 10A, and 5A from Rayovac)
124 Microtronic PJ 88 Volume Control
125 high frequency boost capacitor (Tansitor®)
131 on-board regulator
201 bias resistor (such as a Brill International 47 Ohm resistor)
202 feedback resistor for noise generator (such as a Brill International 10 k ohm resistor)
203 resistor (such as a Brill International 100 Ohm resistor)
206 Receiver (Knowles)
218 output capacitor
219 output isolation capacitor (Tansitor®) (duplication of Vbatt)
227 Monolithic IC High Gain Class A Amplifier
327 Monolithic IC (Two stage) High Gain Class A Amplifier
395 Tansitor® 2.2 microfarad capacitor
397 Tansitor® 0.047 microfarad capacitor
427 Monolithic IC (Two stage) High Gain Class D Amplifier
527 C-MOS amplifier, output stage Class D
627 K-amp programmable integrated circuit, commercially available from Etymotic Research
$C_{IN}$ 220 nano farad capacitor

TABLE 1

Volume control position to output noise level

| VC Set | Gain | Peak Frequency |
|---|---|---|
| On | −5 dB | 10,000 Hz |
| 1/8 On | −4 dB | 2727 Hz |
| 2/8 On | 0 dB | 2720 Hz |
| 3/8 On | 10 dB | 2720 Hz |
| 1/2 On | 13 dB | 2720 Hz |
| 5/8 On | 16 dB | 2800 Hz |
| 3/4 On | 17 dB | 2800 Hz |
| 7/8 On | 19 dB | 2720 Hz |
| 7.5/8 On | 25 dB | 2720 Hz |
| Full-on | 38 dB | 2900 Hz |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

We claim:

1. A tinnitus habituator for managing tinnitus and hyperacusis, said habituator comprising:

a device which fits into a user's ear canal;

said device including a shell and a single noise generator within said shell for generating sounds to be transmitted to the tympanic membrane for treating said tinnitus and hyperacusis; and said device being positioned within said ear canal so as to allow at least a portion of said ear canal to remain open and thus allow ambient sounds to pass through to the tympanic membrane.

2. The habituator of claim 1, wherein said device leaves about 50% of said ear canal open.

3. The habituator of claim 1, further comprising:

an amplifier and receiver within said shell, said amplifier being connected to said noise generator and said receiver being connected to said amplifier; and an acoustic horn formed within said shell for directing sounds from said noise generator to the tympanic membrane.

4. The habituator of claim 3, further comprising means for positioning said device within said ear canal.

5. The habituator of claim 4, wherein:

said positioning means comprises a pair of retention arms; and said retention arms serve to aim said receiver at a superior portion of said tympanic membrane.

6. The habituator of claim 1, further comprising volume control means for adjusting the level of transmitted noise.

7. The habituator of claim 6, further comprising said volume control means having a taper for allowing discrete adjustment of low level sounds while maintaining a stable signal output.

8. The habituator of claim 1, further comprising:

said shell having a faceplate, said faceplate having an opening at the apex of the external ear canal for allowing ambient sound to enter the ear canal; and a medial ipsolateral route of signal vent retainer located at a distal end of the device, said vent retainer supporting said device upward into a superior portion of the external ear canal and at the same time keeping the inferior ear canal open and veritably unobstructed for free-field sound transmission.

9. The habituator of claim 8, further comprising an extraction cord affixed to said faceplate.

10. The habituator of claim 9, wherein said extraction cord serves as a volume control extension which allows adjustment of the noise level generated by said noise generator.

11. The habituator of claim 1, wherein said sound generator comprises a thermal circuit noise generator.

12. The habituator of claim 1, further comprising means for adjusting the volume of the noise generated by said noise generator to 0 dB.

13. The habituator of claim 1, wherein said noise generator comprises means for generating a broad-band low-level signal for stimulating auditory pathways.

14. A tinnitus habituator for managing tinnitus and hyperacusis, said habituator comprising:

a device which fits into the ear canal;

said device including a shell and a single noise generator within said shell for generating a broad-band, low-level signal for stimulating auditory pathways to treat said tinnitus and hyperacusis;

an amplifier and receiver within said shell, said amplifier being connected to said noise generator and said receiver being connected to said amplifier;

an acoustic horn formed within said shell for directing generated noise to a user's tympanic membrane;

volume control means for adjusting the level of transmitted noise, said volume control means having a taper for allowing discrete adjustment of low level sounds while maintaining a stable signal output; and said device being positioned within said ear so as to allow at least a portion of said ear canal to remain open and thus allow ambient sounds to pass through to the tympanic membrane.

* * * * *